United States Patent
Broadfoot

(10) Patent No.: US 9,392,352 B2
(45) Date of Patent: Jul. 12, 2016

(54) WEARABLE APPARATUS

(71) Applicant: Earlug Limited, Glasgow (GB)

(72) Inventor: Stephen Broadfoot, Glasgow (GB)

(73) Assignee: Earlug Limited, Glasgow (GB)

( * ) Notice: Subject to any disclaimer, the term of this patent is extended or adjusted under 35 U.S.C. 154(b) by 0 days.

(21) Appl. No.: 14/404,423

(22) PCT Filed: Jun. 30, 2013

(86) PCT No.: PCT/GB2013/051474
§ 371 (c)(1),
(2) Date: Nov. 26, 2014

(87) PCT Pub. No.: WO2013/179070
PCT Pub. Date: Dec. 5, 2013

(65) Prior Publication Data
US 2015/0189418 A1    Jul. 2, 2015

(30) Foreign Application Priority Data

Jun. 1, 2012 (GB) .................................. 1209763.0
Mar. 7, 2013 (GB) .................................. 1304160.3

(51) Int. Cl.
*H04R 1/10*    (2006.01)
*A61F 11/12*    (2006.01)

(52) U.S. Cl.
CPC ............... *H04R 1/105* (2013.01); *A61F 11/12* (2013.01)

(58) Field of Classification Search
CPC ............ H04R 5/02; H04R 1/02; H04R 1/105; H04R 1/08; H04R 5/0335; H04R 2201/10; H04R 1/025; H04R 1/026
USPC .................. 381/301, 333, 364, 367, 376, 388
See application file for complete search history.

(56) References Cited

U.S. PATENT DOCUMENTS

| | | | | |
|---|---|---|---|---|
| 1,354,524 A | * | 10/1920 | Timmons | 381/376 |
| 4,525,878 A | * | 7/1985 | Lowe, Jr. | 2/209.13 |
| 4,776,044 A | * | 10/1988 | Makins | 381/376 |
| 5,164,987 A | * | 11/1992 | Raven | 381/309 |
| 6,792,124 B2 | * | 9/2004 | Tilbury et al. | 381/333 |
| 7,394,912 B2 | * | 7/2008 | Whipple | 381/376 |
| 7,519,192 B1 | * | 4/2009 | Laycock et al. | 381/301 |
| 8,009,847 B2 | * | 8/2011 | Planansky | 381/301 |
| 8,111,857 B2 | * | 2/2012 | Kuhtz et al. | 381/370 |
| 8,526,658 B1 | * | 9/2013 | Houston | 381/376 |
| 2006/0185062 A1 | * | 8/2006 | Peng et al. | 2/209.13 |
| 2009/0199326 A1 | | 8/2009 | Brauner et al. | |
| 2011/0094007 A1 | | 4/2011 | Brauner et al. | |
| 2011/0116673 A1 | * | 5/2011 | Lewis | 381/376 |

FOREIGN PATENT DOCUMENTS

EP    1449504 A1    8/2004

OTHER PUBLICATIONS

International Search Report for related international application No. PCT/GB2013/051474.

* cited by examiner

*Primary Examiner* — Suhan Ni
(74) *Attorney, Agent, or Firm* — Benesch Friedlander Coplan Aronoff, LLP; Thomas Y. Kendrick

(57) ABSTRACT

A wearable apparatus comprising a body attachment portion configured to attach to a wearer's body part. The wearable apparatus comprises an ear device connected to the body attachment portion by an ear device connection member. In some examples, the apparatus comprises a storage element, configured to store and retain the ear device with the apparatus. In some examples, the body attachment portion is reconfigurable between a first configuration for attachment at a first body part and a second configuration for attachment at a second body part.

15 Claims, 5 Drawing Sheets

WEARABLE APPARATUS

CROSS-REFERENCE TO RELATED APPLICATIONS

This application is a National stage entry under 35 U.S.C. §371 of PCT Patent Application Ser. No. PCT/GB2013/051474, filed Jun. 3, 2013, which claims priority to United Kingdom Patent Application Ser. No. GB 1209763.0, filed on Jun. 1, 2012, and United Kingdom Patent Application Ser. No. GB 1304160.3, filed on Mar. 7, 2013, each of which is hereby incorporated by reference.

FIELD

The present invention relates to wearable apparatus, in particular wearable apparatus comprising an ear device, and associated methods.

BACKGROUND

In environments with high levels of noise, especially environments with high levels of noise of particular frequencies, there may be a risk of damage to the ear. For example, short-term or long-term hearing impediments may arise, such as permanent or temporary noise-induced hearing loss.

High levels of noise can also detract from the enjoyment or accessibility of particular environments.

Ear devices exist that can be of benefit to a wearer. For example, there are ear device products available that allow the wearer to control the level of noise frequencies reaching the ear. Controlling the level of noise frequencies reaching the ear can help protect the ear against damage. However, ear devices are not always worn in environments where they can be of benefit to the wearer.

SUMMARY

According to a first aspect of the present invention, there is provided a wearable apparatus and associated methods.

In particular examples, the apparatus comprises ear devices. Such ear devices may be configured to prevent, or mitigate, damage that would otherwise occur to a person's ear when that person is in noisy areas (e.g. concerts, or the like). Such ear devices may be configured to attenuate acoustic pressure. Providing the ear devices together with the wearable apparatus may increase the ease of use of the ear devices, and so encourage a person to use the devices more frequently, and/or for longer periods of time. For example, such an apparatus may encourage a wearer to use an ear device; and/or limit loss of an ear device (e.g. due to falling out, or being dropped when not in use). Providing such an apparatus may increase the attractiveness of an ear device for a wearer to use. Providing such an apparatus may make insertion/reinsertion of an ear device easier.

In some examples, the apparatus may comprise a body attachment portion configured to attach to a wearer's body part.

The apparatus may comprise an ear device connection member, connecting the ear device to the body attachment portion.

The body attachment portion may be reconfigurable between a first configuration for attachment at a first body part and a second configuration for attachment at a second body part (and potentially further configurations for attachment to a body part).

The apparatus may comprise a pair of ear devices. Each ear device may be connected to the body attachment portion by an ear device connection member (e.g. a discrete ear device connection member).

In some examples, connecting ear devices to a body attachment portion may allow the wearer to store and wear the ear devices conveniently, with less likelihood of the ear devices being lost, giving the wearer different options of where the body attachment can be worn.

The body attachment portion may be flexible.

By providing ear devices connected to a flexible body attachment portion the ear devices may be more likely to be worn to the benefit of the user.

The body attachment portion may comprise a strap.

The body attachment portion may comprise a releasable strap.

The body attachment portion may comprise a first end portion and a second end portion, the end portions being attachable to each other to form a continuous loop.

The body attachment portion may comprise one or more fasteners (e.g. hook-and-loop; and/or buckle; and/or adhesive; and or snap-fit). For example, each end portion may comprise fastener(s), such that the end portions may be fastened to each other (e.g. releasably fastened).

The body attachment portion may be configured to have an adjustable length. For example, the fastener may be adjustable so as to allow the body attachment portion to form a continuous loop with a variable length (e.g. a variable effective circumference from a first effective circumference to a second effective circumference).

The first circumference may be less than 5 cm. The second circumference may be greater than 15 cm. The second circumference may be substantially the full length of the body attachment portion.

The apparatus may be configured to provide an adjustable circumference or length of loop. The apparatus may be adjustable by providing a variable length overlap, for example, of the end portions (e.g. having a region of the apparatus that overlaps, for example when fastened, with a different region of the apparatus).

The loop may comprise the overlap. In other words, at least a portion of the loop may comprise two regions overlapping with one another. In such cases, the overlap may be considered to be substantially concentric with the loop.

The overlap may be a non-loop overlap, such as discrete from the loop. For example, the overlap may be substantially radial or substantially tangential to the loop.

The apparatus may be reconfigurable between a continuous loop (e.g. with a loop overlap) and a pendant shape (e.g. with a non-loop overlap).

The apparatus may be reconfigurable between a continuous loop with an inner and an outer surface and a continuous loop with a single continuous surface comprising an inner and an outer surface (e.g. having a Möbius configuration).

The apparatus may be reconfigurable between at least a first configuration and a second configuration.

The apparatus may be reconfigurable between (i) a first configuration with a loop together with and non-loop-overlap and (ii) a second configuration with a loop together with and loop-overlap. The loop/apparatus may be reconfigurable between a loop comprising an overlap and a loop without an overlap.

The apparatus may be reconfigurable between a single loop configuration and a multiple loop configuration, such as a double and/or a triple loop, etc. The apparatus may be reconfigurable between configurations such that the body attachment portion need not comprise a twist.

The first configuration (e.g. single loop configuration) may be for use as neckwear.

The second configuration (e.g. multiple loop configuration) may be for use as wristwear.

The fastener may be provided at a region of overlap (e.g. comprise at least the length of the overlap). For example, the fastener may comprise an adhesion or attachment means, such as a hook-and-loop fastener, extending substantially along some or the entire length of the intended, expected, or desired, overlap.

The fastener or a plurality of fasteners may be engaged at one or more discrete points along the overlap.

The fastener may extend for a majority of the length of the body attachment portion. For example, the body attachment portion may comprise a hook portion associated with the first end portion and a loop portion associated with a second end portion. The hook and/or loop portion/s may extend for more than half the length of the body attachment portion.

The body attachment portion may comprise a stretchable material.

The body attachment portion may comprise an elastic material.

The body attachment portion may comprise a rip stop material. The body attachment portion may comprise a webbing.

The body attachment portion may comprise a portion configured to receive or display indicia. For example, the body attachment portion may comprise a substantially planar or flat surface, such as receptive to ink or other printing or coloration materials.

The body attachment portion may comprise a release member configured to allow the body portion to be separated at the release member. In some example, the release member may be configured to be a safety release member. For example, the body attachment portion may comprise a safety release member, such as a buckle, or the like, configured to release at a predetermined tension (e.g. to prevent discomfort and/or injury such as strangulation to the wearer).

The release member may be reversible.

The release member may be configured to allow the respective first and second end portions to be coupled such that at least a portion of one of the end portions may be effectively reversed between configurations (e.g. between first and second configurations). Effectively reversing at least a portion of one of the end portions may allow additional configurations, such as a Möbius configuration and/or a loop overlap configuration and a non-loop-overlap configuration.

The apparatus may be configured to protect and/or conceal the ear device(s) and/or the ear device connection member(s) in one or more configurations.

The apparatus may be configured for use by a particular wearer. For example, the apparatus may comprise a wearer-dependent ear device (e.g. an earplug configured to fit the particular wearer's ear) and/or an identification element (e.g. a photo/security badge/pass).

The first configuration may be for use with a first body part, such as a neck. The second configuration may be for use with a second body part, such as a limb, such as an arm (e.g. wrist) and/or a leg (e.g. ankle).

The body attachment portion may comprise one or more an ear device storage elements. The/each storage element may be configured to maintain, retain, and/or store the ear device together with the body attachment portion. The body attachment portion may comprise discrete ear device storage elements for each ear device. The body attachment portion may comprise one or more single ear device storage element/s for a plurality of ear devices.

A fastener and/or ear device connector and/or an ear device storage element may be located on a first side of the first end portion. A second fastener and/or a second ear device connector and/or a second ear device storage element may be located on a first side of the second end portion.

In a first configuration, the first side of the first end portion may be at least partially coincident and/or coplanar with the first side of the second end portion. For example, the first side of the first end portion and the first side of the second end portion may each comprise an interior or inside of a loop. In a second configuration, the first side of one of the end portions may comprise an interior or inside of a loop and the first side of the other end portion may comprise an exterior or an outside of the loop.

The ear device storage element may comprise an ear device attachment member, such as a recess or an opening (e.g. a hole or blind hole) or a pocket and/or a fastening (e.g. a clip, strap, hook, or the like) and/or an adhesive or material (e.g. hook-and-loop or a tacky material or a magnetic material).

The ear device storage element may be formed by the fastener. The ear device storage element may be defined by an open seam or an opening between elements of the apparatus, such as between the fastener and the body attachment portion. For example, the fastener may comprise a portion of hook-and-loop material, attached (e.g. sewn and/or adhered) to a portion, such as the end portion, of the body attachment portion (e.g. a strap); and the ear device storage element may be defined by an open seam or opening along at least one side of the fastener's attachment to the body attachment portion.

The ear device may comprise a fastener for storage on the body attachment portion. For example, the ear device may comprise a portion of hook-and-loop material configured to correspond to a portion of hook-and-loop material on the body attachment portion.

The fastener may comprise the ear device storage element. For example, the ear device may be stored between two portions of the fastener. Where the fastener is of the hook and loop type, the ear device/s may be stored between the hook portion and the loop portion, such as substantially encompassed by the hook portion on one side and the loop portion on the other side.

The ear device may comprise an in-ear device. The ear device may comprise an ear plug, such as an ear plug or bung configured to limit passage of noise of particular frequencies to the ear. The ear device may comprise an ear protector. The ear device may be configured to prevent or impede the passage of sound through an ear canal. The ear device may comprise foam (e.g. compressible foam). The ear device may be a homogenous foam material.

The ear device may comprise a powered ear device.

The ear device may comprise a sound-emitting ear device (e.g. a headphone).

The apparatus may comprise a plurality of types of ear device. For example, the apparatus may comprise an ear plug for use in particular circumstances, and a sound-emitting ear device for use in other circumstances. The apparatus may comprise a plurality of types of ear plug. For example, the apparatus may comprise a plurality of ratings of ear devices, such as a plurality of forms (e.g. diameters) and/or for a plurality of frequency and/or decibel ratings. The apparatus may comprise a plurality of ear devices for different users and/or usage environments.

The ear device connection member may comprise a longitudinal member.

The ear connection member may be flexible.

The ear device connection member may comprise a plastic connector and/or wire (e.g. an electrically conductive wire).

The ear device connection member may comprise a tether.

The ear connection member may be attached to the body attachment portion. The ear connection member may be permanently mounted to the body attachment portion. The ear connection member may be releasably attached to the body attachment portion. The ear connection member may be replaceable. The ear connection member may be attached to the body attachment portion at a connection or anchor point. The anchor point may be located proximal to the fastener. The anchor point may be located distal to the fastener. The anchor point may be located proximal to the safety release member. The anchor point may be located proximal to the safety release member. The anchor point may be located distal to the ear device storage element. The anchor point may be located proximal to the ear device storage element. The anchor point may be located at or in the ear device storage element.

The ear connection member may be configured to have a substantially fixed length.

The ear connection member may comprise a length such that it can extend between the anchor point and the ear device storage element, in use. The ear connection member length between the anchor point and the ear device storage element may substantially correspond to a length of the body attachment portion extending between the anchor point and the ear device storage element. The apparatus may be configured such that when the ear device is stored in the ear device storage element, the ear device connection member is substantially coincident with and/or adjacent to and/or collinear with and/or of similar (e.g. equal) length to a corresponding portion of the body attachment portion (such as a strap portion) extending between the ear device storage element and the anchor point.

The ear connection member may comprise a variable or adjustable length. The ear connection member may comprise an adjustable length from the anchor point to the ear device. For example, the ear device connection member may be slidably attached at the anchor point. A reserve or redundant length of connection member may be provided, such as located or stored behind the anchor point. An effective length of the connection member may be adjusted by using a variable amount of reserve length.

The ear device connection member may be substantially inelastic.

The ear device connection member may be elastic.

The apparatus may comprise, or be configured at least in one configuration, as a lanyard.

The apparatus may be configurable as wristwear. The apparatus may comprise a bracelet.

The apparatus may be configurable as neckwear.

The apparatus may be configurable as torsowear. The apparatus may be configurable as a waistband or a belt or braces or the like.

The apparatus may be configurable as headwear; such as a hat, a cap, a bandana, a visor, or the like.

The apparatus may be reconfigurable between wristwear and/or neckwear and/or headwear and/or torsowear.

The apparatus may comprise a security element. The apparatus may be configured to enable access; such as access to an event and/or a venue and/or a restricted area and/or a restricted service and/or equipment. The security element may comprise an identifier, such as a unique identification code. The security element may comprise a visual element (such as photographic) and/or an electronic element (such as a chip) and/or an electronically-readable element (such as a bar code, a smart code, an RFID tag or the like).

The apparatus may comprise an attachment portion for an auxiliary apparatus. For example, the apparatus may comprise an auxiliary fastener. The auxiliary fastener may comprise an eyelet, a clip, a hook, a karabiner, a key ring, or the like. The auxiliary apparatus may comprise the security element; a key; a microphone; an ID reader; glasses; or the like.

The apparatus may be disposable.

The apparatus may be a single-use apparatus. The apparatus may be degradable, such as biodegradable. The apparatus may be configured to indicate use, such as a first use. The apparatus may comprise a usage indicator. The usage indicator may be a visual indicator. For example, the apparatus may comprise a transient colour. The apparatus may be configured to change colour when used. For example, the apparatus may comprise a temperature-sensitive and/or moisture-sensitive and/or atmosphere-sensitive and/or light-sensitive and/or time-dependent material, such as a chronochromatic fabric.

The apparatus may be reusable.

The ear device/s may be storable and/or wearable (e.g. in-ear) in one or more of the configurations. The ear device/s may be storable and/or wearable (e.g. in-ear) in all of the configurations.

According to a further aspect of the invention, there is provided a method of attaching wearable apparatus comprising an ear device to a wearer's body. The method may comprise attaching the apparatus in different configurations (e.g. on a first body part, and then on a second body part).

The method may comprise providing a wearable apparatus comprising an ear device connected to a body attachment portion of the apparatus by a connection member, and attaching the body attachment portion to a first body part. The method may comprise detaching the body attachment portion and reconfiguring the body attachment portion. The method then may comprise attaching the reconfigured body attachment portion to a second body part.

The method may comprise reconfiguring the body attachment portion between a single loop configuration and a multiple loop configuration.

The method may comprise winding the body attachment portion around at least one of the body parts.

The method may comprise helically winding the body attachment portion.

The method may comprise substantially concentrically winding the body attachment portion.

According to a further aspect of the invention, there is provided a wearable apparatus comprising a body attachment portion configured to attach to one or more body parts of a wearer.

The apparatus may comprise one or more ear devices.

The apparatus may comprise one or more ear device connection member, connecting each ear device to the body attachment portion.

The body attachment portion may comprise one or more ear device storage elements.

According to a fourth aspect of the invention there is provided a method of controlling group or audience exposure to sound (e.g. potentially harmful acoustic pressure).

The method may comprise identifying at least one region or zone associated with a particular potential sound exposure profile (e.g. having acoustic pressure in excess of a particular power level (e.g. dB)).

The method may comprise limiting access to the region or zone.

The method may comprise preventing or at least mitigating potential exposure or overexposure to sound levels, such as potentially damaging decibel and/or frequency level/s.

The method may comprise identifying a plurality of regions or zones, each region or zone being associated with a particular potential sound exposure profile. The method may comprise prescribing an appropriate wearable apparatus comprising an ear device (e.g. as per any of the above aspects/features) to the/each zone or region.

In some examples, the method may comprise rating the appropriate wearable apparatus to correspond to the particular potential sound exposure profile.

The regions or zones may be located within the same environment, such as a same room or space. For example, the regions or zones may be located within a same performance or concert venue, such as an arena.

The regions or zones may be located within different environments.

The method may comprise monitoring the region/s or zone/s to check for compliance. The method may comprise identifying non-compliant person/s in the zone/s or region/s. The method may comprise alerting the non compliant person/s. The method may comprise displacing the non-compliant person/s, such as from the region or zone.

The method may comprise providing a visually distinguishable wearable apparatus (e.g. a particular colour). The method may comprise providing a radiation-responsive wearable apparatus. For example, the method may comprise emitting a particular wavelength (such as ultraviolet light or low power UV-A) to highlight the wearable apparatus.

The method may comprise measuring sound at one or more locations within the/each zone or region. The method may comprise measuring relative sound levels at a plurality of locations within the/each zone or region.

The method may comprise identifying the zone/s or region/s dependent upon a predetermined parameter. The predetermined parameter may comprise a distance from a sound source; and/or an acoustic property of an intermediate and/or surrounding environment (e.g. a reflective property of a venue) relative to the region or zone; and/or an acoustic property of an intermediate medium (such as a mass or anticipated mass between a location and the sound source).

According to a fifth aspect of the invention there is provided an array of wearable apparatus.

Each wearable apparatus may comprise an ear device of differing rating or specification. For example each apparatus may be configured to provide protection from a different volume and/or frequency range of sound.

Each wearable apparatus may comprise a different security element. For example, each apparatus may comprise an identifier (e.g. a colour of a body attachment portion) corresponding to access to a different region or zone.

The invention includes one or more corresponding aspects, embodiments or features in isolation or in various combinations whether or not specifically stated (including claimed) in that combination or in isolation. For example, it will readily be appreciated that features recited as optional with respect to the first aspect may be additionally applicable with respect to the other aspects without the need to explicitly and unnecessarily list those various combinations and permutations here.

In addition, corresponding means for performing one or more of the discussed functions are also within the present disclosure.

It will be appreciated that one or more embodiments/aspects may be useful in providing wearable apparatus, such as comprising an ear device.

The above summary is intended to be merely exemplary and non-limiting.

BRIEF DESCRIPTION OF THE FIGURES

These and other aspects of the present invention will now be described, by way of example only, with reference to the accompanying drawings, in which.

DETAILED DESCRIPTION:

Particular non-limiting features of the following described embodiment include:
1. Body attachment portion—device that attaches to body.
2. Fastening material 'a'—combines with 'fastening material 'b'' (3) to secure 'body attachment' (1).
3. Fastening material 'b'—combines with 'fastening material 'a'' (2). to secure 'body attachment' (1).
4. Ear device—e.g. ear inserts controlling noise level frequencies.
5. Connecting member—member attaching 'ear device' (4) to 'body attachment' (1).
6. Connection point—point where 'connecting member' (5) attaches to 'body attachment' (1).
7. Storage element—e.g. pocket of 'body attachment' (1) for 'ear device' (4) storage.
8. Release member—e.g. a safety break buckle that stops chock hazard of 'body attachment' (1).

Figure 1:
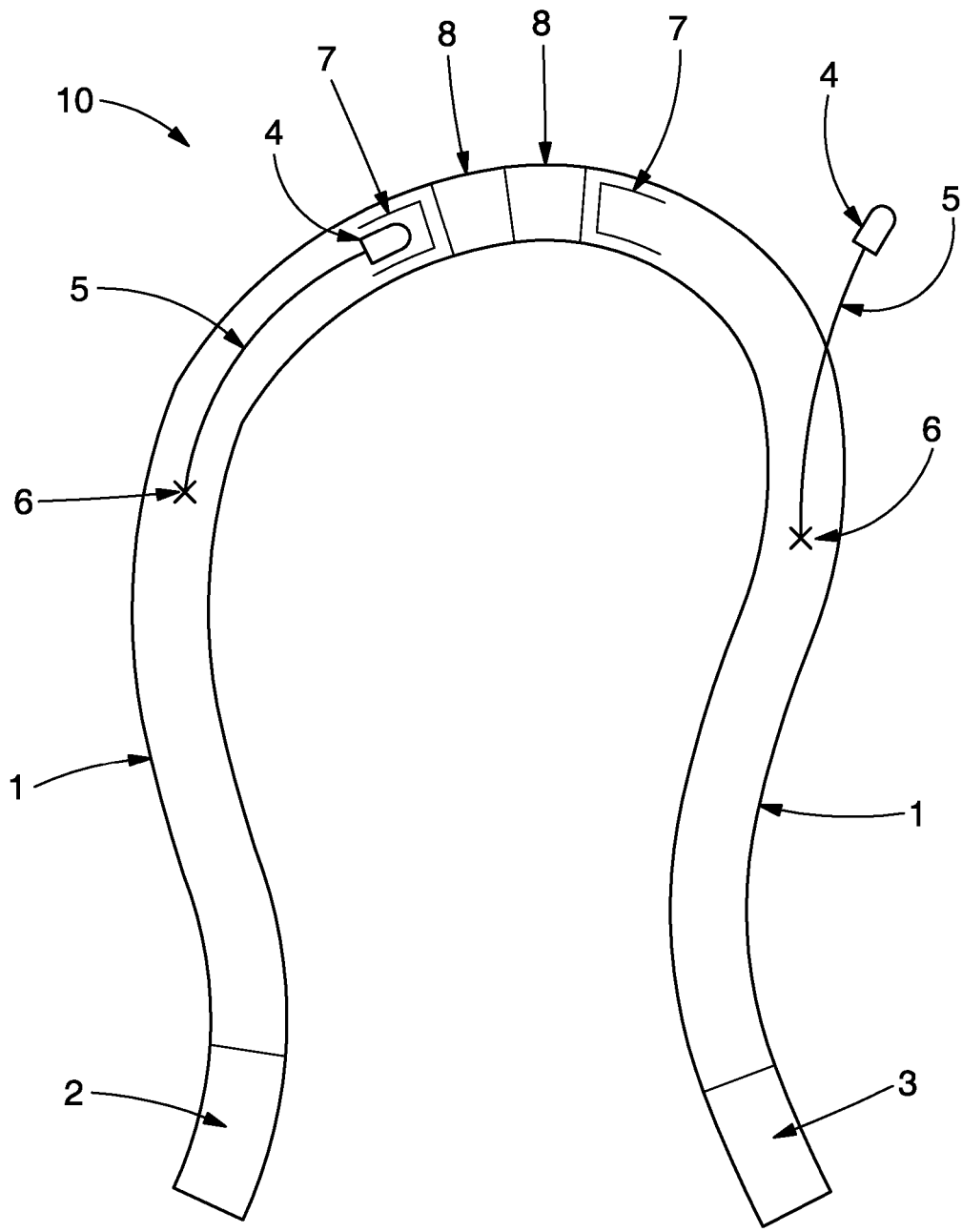
FIG. 1 shows a wearable apparatus 10 according to an embodiment of the present invention.

FIG. 1 shows an example of wearable apparatus 10 according to a first described embodiment. The apparatus 10 is wearable on a user, as will be described, and can help increase the ease of use of ear devices, such as foam or silicon earplugs. In this example, the apparatus 10 may be considered to be generally resemble a lanyard.

The apparatus 10 described can help encourage a person to use those ear devices more frequently, and/or for longer periods of time. For example, the apparatus 10 may encourage a wearer to use an ear device; and/or limit loss of an ear device (e.g. due to falling out, or being dropped when not in use). The described apparatus 10 may additionally increase the attractiveness of an ear device for a wearer to use, as well as making any insertion/reinsertion of an ear device easier.

The apparatus 10 comprises a body attachment portion 1. In this example, the body attachment portion can be secured (e.g. removably secured) to a wearer's body by using fasteners, such as fastening means or materials 'a' 2 and 'b' 3, as will be described. While in the following examples, fastening material, as such (e.g. loop-and-hook material), has been described, it will readily be appreciated that other suitable fasteners may be used, not least of all complementary press studs, magnets, clips, etc. A skilled reader will readily be able to implement those further embodiments accordingly.

In some cases, the fasteners (e.g. loop-and-hook material) are positioned along some or all of the apparatus (i.e. along some or all of the length of the body attachment portion 1). For example, in some cases, fastening material, or the like, is provided along the entire length of the apparatus (either continuously, or discontinuously), such that one side of the apparatus can be secured to the other at various user-desired lengths. Such a configuration may permit ease of wearing between different users, and/or different positions on a wearer (e.g. at a neck region, and/or at a wrist region).

Here, two ear devices 4 are connected to the body attachment portion 1 via connecting members 5. It may be considered that each member 5 extends between a connecting point 6 and an ear device 4. As will be explained, the ear device 4 is stored or at least retained with the body attachment portion 1 by using a storage element 7. In some examples, the storage element 7 is specifically configured to store and retain the ear device 4 itself (e.g. in the form of a complementary pocket). However, in further examples, the storage element 7 may be configured to store/retain a portion of the connecting member 5, such that the ear device 4 is stored/retained together with the body attachment portion 1. Either way, the apparatus 10 is configured such that the ear device 4 has a stowed configuration, and an in-use configuration. In the stowed configuration, the ear device 4 is retained with the body attachment portion 1 (e.g. by placing the ear device in pocketed storage element 7, or the like). In the in-use configuration, the ear device 4 is free to be placed in a user's ear. In such examples, it is generally the case that the ear device 4 remains attached to the apparatus 10 via the connecting member 5, and so mitigates accidental loss of that device 4. However, in some examples, the apparatus may comprise ear devices 4 not connected via connecting members 5, yet still stowable using storage elements.

Here, the ear device 4 is be stored in a pocket 7, or other retaining means (e.g. other storage elements), when not in use. In this example, the connecting member 5 is flexible to allow for ease of use.

In this particular example, although not in all examples, the body attachment portion 1 comprises a release member 8, which is configured to separate the body attachment portion 1. In this particular case, the release member 8 is configured as a safety break buckle 8 that allows for the removal of any choke hazard under stress pull. In other words, the member 8 can be separated by using a person force pulling on the body attachment portion 1, without the need to activate or press in some way the release member 8.

In the example shown, the storage element 7, which is exemplified as a pocket 7, or retaining means, is positioned proximate that release member 8, and distal from the connecting point 6. However, in other examples (e.g. see FIG. 2a), the apparatus 10 may be configured such that the storage element 7, pocket, or retaining means, etc. is positioned on the other side of the connecting point 6, away from the release member 8. Such a configuration may permit ease of use, when the apparatus 10 is configured such that the release member is positioned at a neck region (e.g. at the back of the neck) or a user/wearer.

Figure 2A:
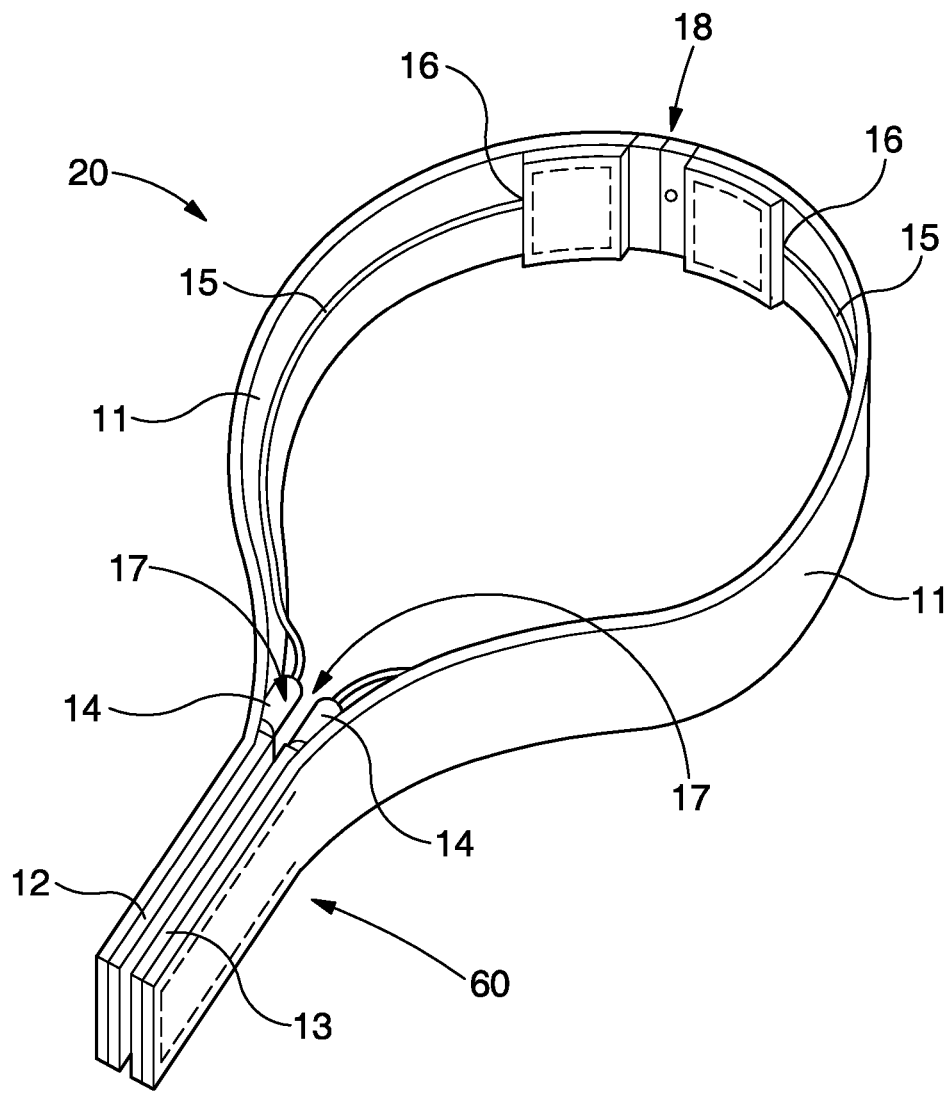
FIG. 2a shows a wearable apparatus in accordance with an embodiment of the invention in a first configuration.

FIG. 2a shows an alternative embodiment of the apparatus 20 generally similar to the apparatus 10 shown in FIG. 1, and as such like features share like reference numerals, incremented by 10. Here, the apparatus 20 can be considered to be shown in a first configuration. Again, the apparatus 20 comprises a body attachment portion 11 securable to a wearer's body using fasteners (e.g. fastening means or materials a 12 and b 13. The apparatus 20 shown in FIG. 2a can be considered to be in a pendant configuration. The configuration of FIG. 2a may permit wearing of the apparatus 20 as a lanyard (e.g. around the neck of a wearer).

The body attachment portion 11 comprises a portion or surface configured to receive or display indicia (e.g. logos, or the like). In the embodiment shown, the body attachment portion 11 comprises a strap with a surface (e.g. a substantially planar or flat surface) that is receptive to ink or other printing or coloration materials. Such indicia may be used to provide promotional or advertising information, and/or may be used to provide safety information (e.g. instruction for use of the apparatus).

In this first configuration, the apparatus 11 defines an overlap 60 that is discrete from a loop formed by the body attachment portion 11. The overlap 60 is substantially radial to the loop. The apparatus 20 may be worn by a user, such as around a neck. The apparatus 20 may be put on or removed by separating the fasteners (e.g. fasteners means or materials a 12 and b 13); and reattaching by the fasteners (e.g. fastening means or materials a 12 and b 13). The circumference of the loop may be adjusted by varying the amount of overlap 60 of the fastener.

In use, the apparatus 20 may comprise a sufficient diameter of loop for application over a wearer's head. Alternatively, the apparatus 20 may be applied to the wearer by releasing the fastening means or materials a 12 and b 13. The body attachment portion 11 may then be wrapped around the wearer (e.g. head, neck or waist), such as to be comfortable. The fastening means or materials a 12 and b 13 may be fastened to provide a suitable overlap 60. Additionally or alternatively, the release member 18 may be used to release and fasten the apparatus 20 around the wearer (e.g. at the back of the neck). In this first configuration, the body attachment portion 11 may be considered to comprise a substantially continuous inner surface; such as without any twist in the body attachment portion 11. Providing a substantially continuous inner surface may ensure comfort to the wearer. The absence of any twist may prevent any stress concentration.

In the embodiment shown, ear devices 14, such as foam or silicon earplugs, are configured to prevent, or mitigate, damage that would otherwise occur to a person's ear when that person in noisy areas (e.g. concerts, or the like). The ear devices 14 may be conformable to the shape of an ear canal to ensure an interference fit. The ear devices 14 may comprise plugs of rubber, or foam or the like. Here, the devices 14 have flexible flanges to adapt to the diameter and form of the wearer's ear. In other embodiments, other materials may be used, such as plastics, or the like. Each of the ear devices 14 have a gripping portion facilitating removal. In the embodiment shown, the ear devices 14 have stems. It will be appreciated that the connection members 15 may be used to retrieve the ear devices 14.

Here, the ear devices 14 may be stored with the storage elements 17, which again in this example are shown as pockets; and/or both or singly worn, such as in-ear. It will be appreciated that while pockets have been described, as above, other storage elements 17 may be used. For example, a recess or an opening (e.g. a hole or blind hole) in the body attachment portion may be used to locate and store the ear device, when not in use. Such openings in the body attachment portion 11 may be easy to manufacture. In alternative examples, other storage elements 17 may be used, such as straps spanning across the body attachment portions 11, under which the ear device 14, and/or connecting member 15 may be passed, so as to store/retain the ear devices 14 with the body attachment portion when not in use (e.g. when in a stowed configuration).

Figure 2B:
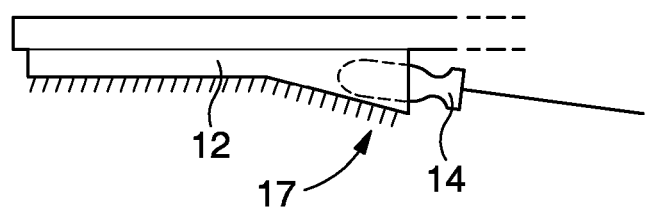
FIG. 2b shows a cross section of a storage element.

In this particular example, the ear device storage element (and in particular the pocket) can be considered to be defined by an open seam or an opening between elements of the apparatus, such as between the fastener 12, 13 and the body attachment portion 11. FIG. 2b shows a cross-section of one end portion of the body attachment portion 11 together with the fastening material 12, showing the storage element 17 of the ear device 14, defined between the fastening material 12 and the body attachment portion 11.

Here, the fastener 12 comprises a portion of hook-and-loop material, attached (e.g. sewn and/or adhered) to the body attachment portion 11. The ear device 14 storage element 17 is defined by an open seam or opening along at least one side of the fastener's attachment to the body attachment portion 11. In other words, the pockets 14 shown in FIGS. 2a and 2b are formed by leaving an opening between the fastening means or materials a 12 and b 13 and the material or strap of the body attachment portion 11. In the embodiment shown, the fastening means or materials a 12 and b 13 are discontinuously stitched or adhered such that a non-attached edge or periphery of the fastening means or materials a 12 and b 13 provides an opening for receiving the ear device 14. Such a configuration also permits ease of manufacture.

In some examples, such as those when not using fasteners 12, 13 (e.g. the body attachment portion 11 is essentially continuous), then the storage elements 17, rather than being formed or defined between the fastener 12, 13 and the body attachment portion 11, may in the alternative be formed between additional material and the body attachment portion 11, which may be used to form a pocket. In some examples, that additional material may be provided by an end of the body attachment portion 11, during manufacture, having being folded back on itself, and stitched or otherwise adhered along the sides in a similar manner, leaving an unstitched or adhered opening for insertion of the ear devices 14, when not in use. A skilled person will readily be able to implement such alternative embodiments.

While use of a pocket has been described essentially as a blind recess, having one opening, it will be appreciated that in further examples the pocket may be configured differently. For example, the pocket may additionally have one or more further openings (e.g. at the other end of the pocket). For example, providing a pocket with an additional opening at the other end may allow the pocket to deform more easily and so allow for ease of introduction of the ear device 14, as well as reduced manufacturing costs. A skilled reader will readily be able to implement these further embodiments.

In this particular embodiment, the connection members 15 are provided by substantially inelastic wires or cables. The connection members 15 are fixed to the body attachment portion 11 at the connection points 16. Of course, in other embodiments, elastic connection members or connection members with adjustable lengths may be provided.

Here, the connection members 15 comprise a length that extends between the connection points 16 and the ear device storage elements 17, when in a stowed configuration. In the shown example, the length of the connection member 15 between the respective connection points 16 and the ear device storage elements 17 substantially corresponds to a length of the body attachment portion 11 extending between the respective connection points 16 and the ear device storage elements 17. If stowed, when the ear devices 14 are stored in the ear device storage elements 17, the respective ear device connection members 15 are substantially coincident with and collinear with a corresponding portion of the body attachment portion 11 extending between each ear device storage element 17 and each connection point 16. However, when required for use, the stored ear devices 14 can be removed from the respective storage elements 17, and placed in the user's ears. In that use, the connection members 15 mitigate the possible loss of the ear devices 14.

Figure 3:
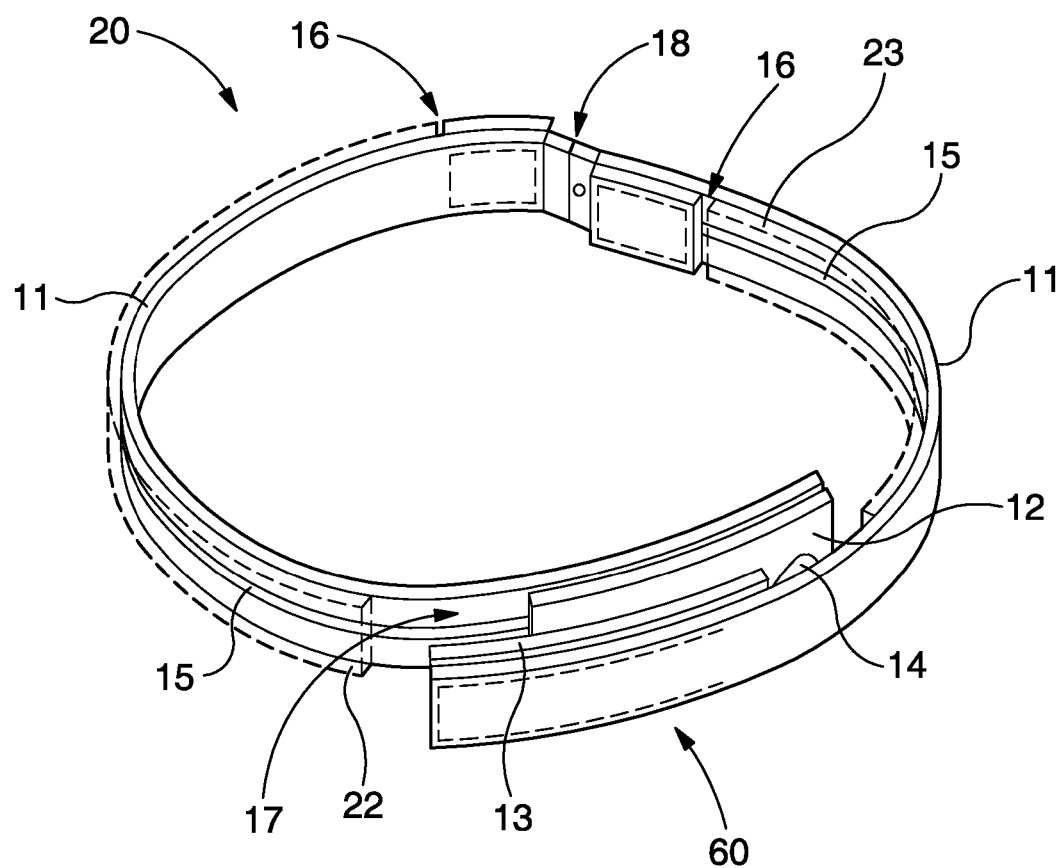
FIG. 3 shows the apparatus of FIG. 2 in a second configuration.

FIG. 3 shows the apparatus of FIG. 2 in a second configuration. One end portion of the body attachment portion 11 has been reversed relative to the configuration of FIG. 2. In the embodiment shown, reversal is attained by unclipping the release member 18 and reconnecting the release member 18 with a portion reversed. Of course, in examples without such a member 18, the apparatus may be twisted by the wearer, or there may be provided a pivot coupling permitting one reverse one end portion relative to the other.

Accordingly, the two connection points 16 shown are on an inside and an outside of the loop respectively. The body attachment portion 11 comprises a single continuous loop. The loop comprises the overlap 60, but in this example the overlap 60 is substantially concentric with the loop in the configuration of FIG. 3. Providing such a continuous loop without any twist may provide increased comfort for the wearer in the further configuration.

In some embodiments, for example, where the fasteners extend most or all of the length of the apparatus then, in essence, first and second possible intermediate fastening portions 22, 23 are provided, and located between the release member 18 and the end portions of the body attachment portion 11. FIG. 3 shows such portions in dashed lines. The intermediate fastening portions 22, 23 may provide for increased adjustability, such as of length and/or circumference of loop and/or of number of loops.

In the embodiment shown with broken lines, the intermediate portions 22, 23 can be considered to provide fastening in addition to the fastening provided at the end regions of the device. In some examples, the respective intermediate portions 22, 23 may comprise the same fastening materials a and b as the respective adjacent fastening means or materials a 12 and b 13.

For example, the first intermediate portion 22 and the first fastening means or materials a 12 may both comprise a hook material; and the second intermediate portion 23 and the second fastening means or materials b 13 both comprise a loop material. However, in other embodiments, the respective intermediate portions 22, 23 may comprise a different, such as opposite, fastening material a and b as the respective adjacent fastening means or materials a 12 & b 13, as will be appreciated.

The configuration of the apparatus 20 as shown in FIG. 3 may allow wearing as a belt and/or a collar and/or a bandana and/or a headband.

In use, the apparatus 20 may be reconfigured to the configuration of FIG. 3, such as from the configuration of FIG. 2, by separating the end portions of the body attachment portion 11 by unfastening the fastening means or materials a 12 & b 13 and/or by releasing the release member 18. The end portions of the body attachment portion 11 may be reattached with one of the end portions reversed relative to the other using the safety buckle 18, which is reversible in the embodiment shown. The body attachment portion 11 may be wound around the wearer, such as around the wearer's neck like a collar. The body attachment portion 11 may be concentrically wound such that the body attachment portion 11 forms a single continuous loop. The body attachment portion 11 may be wound to a comfortable diameter of loop. The fastening means or materials a 12 and b 13 may be fastened so as to form an overlap 60 as part of the loop.

In the second configuration, the body attachment portion 11 may comprise a substantially continuous inner surface; such as without any twist in the body attachment portion 11. Providing a substantially continuous inner surface may ensure comfort to the wearer. The absence of any twist may prevent any stress concentration.

Figure 4:
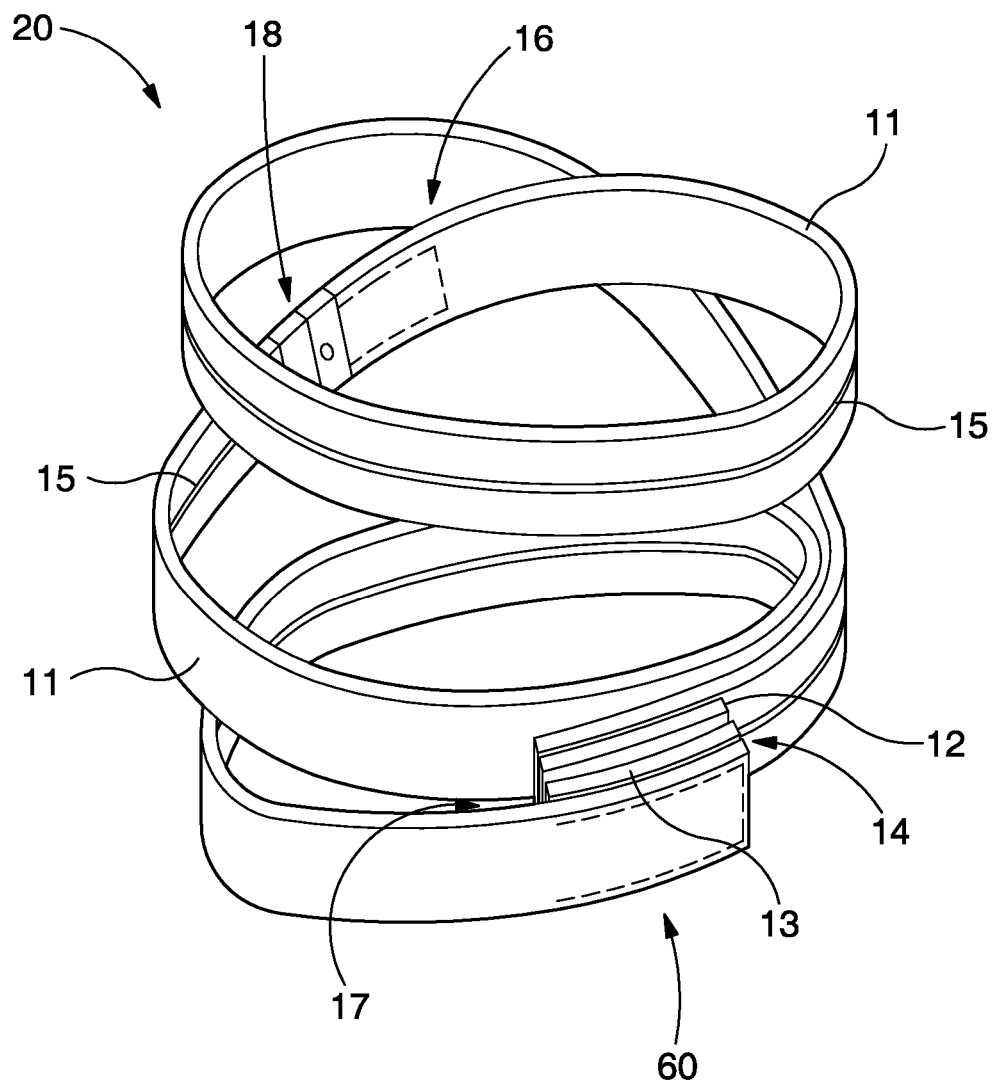
FIG. 4 shows the apparatus of FIG. 2 in a further configuration.

FIG. 4 shows the apparatus 20 of FIG. 2 (and FIG. 3) in a further configuration. The configuration shown comprises a plurality of loops (in this example three are shown, but more may be provided). The plurality of loops comprise a single continuous inside and a single continuous outside. There is no twist, such that a wearer may experience increased comfort. The configuration may permit wearing as wristwear.

In use, the apparatus 20 may be reconfigured to the configuration of FIG. 4, such as from the configuration/s of FIGS. 2 and/or 3, by separating the end portions of the body attachment portion 11 by unfastening the fastening means or materials a 12 and b 13 and/or by releasing the release member 18. The end portions of the body attachment portion 11 may be attached with one of the end portions reversed relative to the other using the release member 18, which is reversible in the embodiment shown. The body attachment portion 11 may be wound around the wearer, such as around the wearer's wrist. The body attachment portion 11 may be helically wound such that the body attachment portion 11 forms multiple loops; which is three in the particular embodiment shown in FIG. 4. The body attachment portion 11 may be wound to a comfortable diameter of loops. The loops may be of similar diameter, corresponding to a diameter of the wearer's wrist. The fastening means or materials a 12 and b 13 may be fastened so as to form an overlap 60 as part of at least one of the loops.

In the configuration of FIG. 4, the body attachment portion 11 may comprise a substantially continuous inner surface; such as without any twist in the body attachment portion 11. Providing a substantially continuous inner surface may ensure comfort to the wearer. The absence of any twist may prevent any stress concentration.

Figure 5:
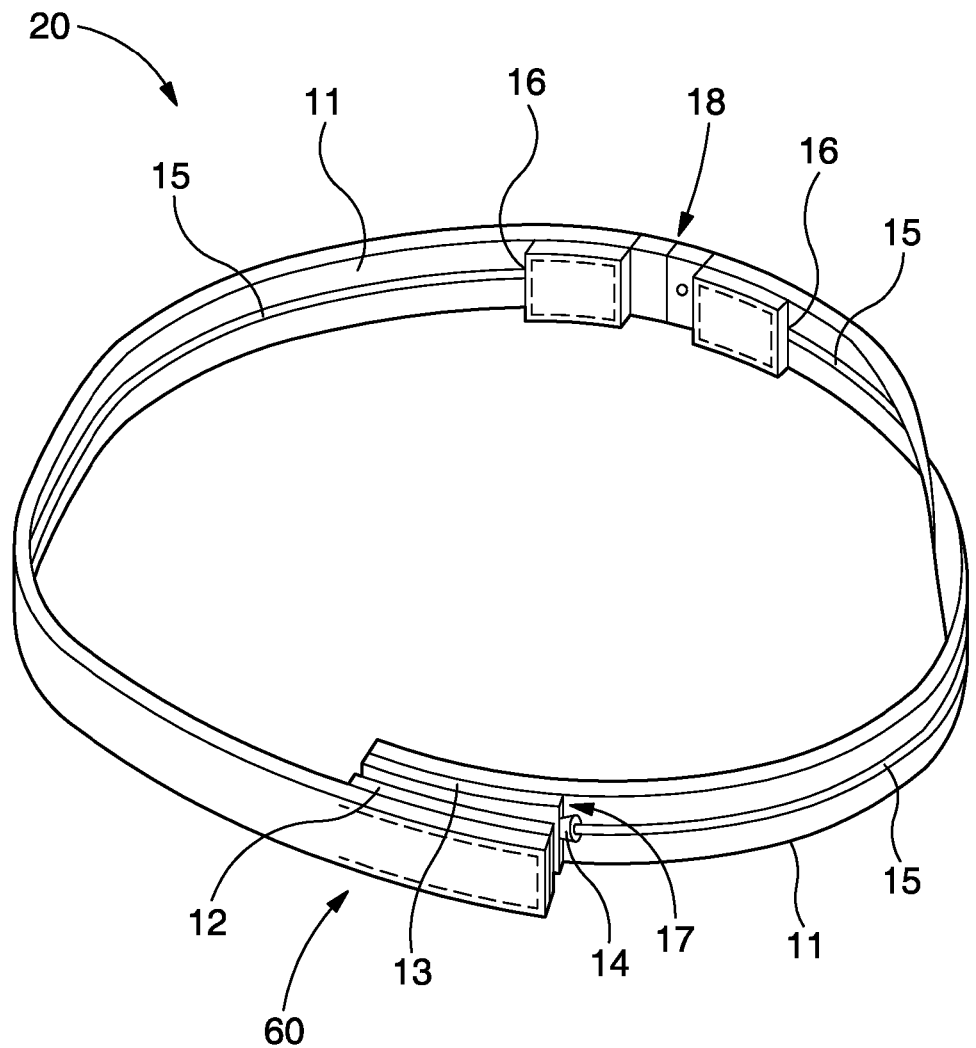
FIG. 5 shows the apparatus of FIG. 2 in another configuration.

FIG. 5 shows the apparatus 20 of FIG. 2 in another configuration. The apparatus 20 comprises a continuous loop with a single continuous surface comprising an inner and an outer surface, in the form of a Möbius strip in the embodiment shown. Such a configuration may allow an overlap forming part of the loop. In the embodiment shown, both connection points 16 are located on a same side of the loop (the inside is shown in FIG. 5); whilst the first fastening means or materials 'a' 12 is also located on the same side (inside) and the second fastening means or materials 'b' 13 is located on an opposite side (outside). Accordingly, the apparatus 20 may be worn with the overlap forming part of the loop, for example, as a collar or belt; whilst both connection points 16 are concealed, such as for protection when not in use in-ear. Alternatively, both connection points 16 could be located on the outside in a reversed configuration of FIG. 5; such as to allow easier access to the connection members 15.

In use, the apparatus 20 may be reconfigured to the configuration of FIG. 5, such as from the configuration/s of FIGS. 2 and/or 3 and/or 4, by separating the end portions of the body attachment portion 11 by unfastening the fastening means or materials a 12 & b 13 and/or by releasing the safety buckle 18. The end portions of the body attachment portion 11 may be attached with the end portions aligned relative to each other (e.g. both connection points 16 may be located on the inside or the outside of the body attachment portion 11), such as using the safety buckle 18. The body attachment portion 11 may be wound around the wearer, such as around the wearer's waist.

In the configuration of FIG. 5, the body attachment portion 11 may comprise a substantially continuous single inner and outer surface; such as with a single twist in the body attachment portion 11. Providing a single twist may allow the location of common features, such as the pair of ear devices 14 or connection points 16 or more of features, such as surfaces for displaying indicia (e.g. advertising) on the outside (or inside) of a loop.

It will readily be appreciated that the embodiment described in relation to FIG. 1 may also provide the configurations of any of FIG. 3, 4 or 5.

In use, the apparatus 10, 20 may be used in the control of exposure of a wearer (e.g. of a group or audience) to sound (e.g. potentially harmful acoustic pressure). By providing a wearable apparatus 10, 20 that permit storage (e.g. retention) of ear devices, the wearer is more likely to continue to wear the apparatus when not in use, and also mitigates the chance of losing the ear devices.

Additionally or alternatively, the wearer may be able to provide the first configuration, and wear the apparatus around their neck when using the ear devices, and then configured the apparatus into, for example, the configuration shown in FIG. 4 so as to be around the wearer's wrist when not in use. The multiple configurations permit the wearer to be able to select an appropriate configuration depending on their needs.

In some examples, the apparatus may additionally be configured to attach a further badge, pocket, or such accessory. For example, the apparatus 10, 20 may be configured with an accessory retainer (e.g. a loop formed in the body attachment portion). In some examples, the accessory retainer may be formed to permit a carabineer, or other such attachment mechanism, to clip to the apparatus, and so attach a security badge, ticket pocket, or the like (e.g. in events or areas having with restricted access).

It will be appreciated that while, by way of an example, the various embodiments have been described having a release member, fasteners, or a body attachment portion provided essentially as a strap or band, in other embodiments any of these features may be omitted. For example, in other embodiments the body attachment portion may comprise a single continuous device, without release member and/or without fasteners, but still having ear devices, for example, connected by connection members, and storage elements for the ear devices.

Further, in alternative embodiments the body attachment portion 1, 11 may be provided by an alternative form of wearing device, such as a head wear (e.g. cap), glasses, or the like, having ear devices connected by connection members, and storage elements for the ear devices. A skilled reader will readily be able to implement those further embodiments.

The above described embodiments may have particular use in, for example, music event, or the like, in which a large number of people gather to listen to music. In those cases, the above described apparatus 10, 20 may be distributed to persons attending such events so that they can protect the ears against harm. In some cases, the apparatus may be made so that it is readily disposable (e.g. biodegradable).

At such events, it may be that a person closer to a stage will experience higher levels of noise (and so potential damage/harm to their ears). In some cases, it may be used to identify at least one region or zone associated with a particular potential sound exposure profile (e.g. having acoustic pressure in excess of a particular power level (e.g. dB)). Then, access to the region or zone may be limited. A plurality of regions or zones may be identified, with each region or zone being associated with a particular potential sound exposure profile. An appropriate wearable apparatus 10, 20 comprising ear devices 4, 14 may be prescribed for each zone or region. Different embodiments of wearable apparatus 10, 20 may be rated to correspond to a particular potential sound exposure profile.

The regions or zones may be located within the same environment, such as a same room or space. For example, the regions or zones may be located within a same performance or concert venue, such as an arena. In other uses, the regions or zones may be located within different environments. In some cases, only a single zone may be identified, within which a wearer is required to use the apparatus 10, 20 described.

The regions or zones may be monitored to check for compliance. Non-compliant persons may be identified in a zone;

and alerted. The person may be issued with a wearable apparatus 20 comprising an ear device 14 to enable compliance. Alternatively, the non-compliant person may be displaced from the region or zone.

In use, the potential exposure or overexposure of any persons, group members or audience members to sound levels, such as potentially damaging decibel and/or frequency level/s may be prevented or at least mitigated.

In some embodiments, it may be appropriate to provided an array of wearable apparatus (e.g. as per any of the above aspects/embodiments). Each wearable apparatus of the array comprises an ear device of differing rating or specification. In some embodiments of the array, each apparatus is configured to provide protection from a different volume and/or frequency range of sound.

In some of the embodiments, each wearable apparatus comprises a different security element. For example, each apparatus may comprise an identifier (e.g. a colour of a body attachment portion) corresponding to access to a different region or zone.

The above described ear devices 4, 14 are specifically configured to reduce or attenuate the acoustic transmission to a wear's ear. Generally, such ear devices 4, 14 can be considered passive (e.g. not powered, such as using foam). However, in some cases, the devices 14 may be active (e.g. using noise cancelling technology). In some examples, features of the above described apparatus 10, 20 (e.g. storage elements, fasteners, etc.) may be used with powered ear devices that comprise earphones or earbuds. A skilled reader will readily be able to use those further embodiments accordingly.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. It should be understood that the embodiments described herein are merely exemplary and that various modifications may be made thereto without departing from the scope of the invention.

The invention claimed is:

1. A wearable apparatus comprising:
    a body attachment portion configured to attach to a wearer's body part;
    an ear device;
    an ear device connection member, connecting the ear device to the body attachment portion; and
    an ear device storage element, configured to store and retain the ear device with the apparatus, when not in use;
    wherein the ear device connection member is attached to the body attachment portion at an anchor point, the anchor point being located distal to the ear device storage element, and wherein the apparatus is configured, in at least one configuration, as a lanyard.

2. The apparatus of claim 1, wherein the storage element is configured as a pocket.

3. The apparatus of claim 2, wherein the pocket is defined using the body attachment portion.

4. The apparatus of claim 3, wherein the pocket is defined between the body attachment portion and a fastener of the apparatus.

5. The apparatus of claim 1, wherein the body attachment portion is reconfigurable between a first configuration for attachment at a first body part and a second configuration for attachment at a second body part.

6. The apparatus of claim 5, wherein the body attachment portion comprises a strap.

7. The apparatus of claim 5, wherein the body attachment portion comprises a releasable fastener, configured to allow for reconfiguration between the first configuration and the second configuration.

8. The apparatus of claim 5, wherein, in the first configuration, the body attachment portion is configured to attach to a neck of a wearer.

9. The apparatus of claim 5, wherein, in the second configuration, the body attachment portion is configured to attach to a limb of a wearer.

10. The apparatus of claim 1, wherein the ear device comprises an ear plug configured to limit passage of noise to a wearer's ear.

11. The apparatus of claim 1, wherein the ear device comprises a powered ear device, including earphones.

12. The apparatus of claim 1, wherein the apparatus is disposable.

13. The apparatus of claim 1, wherein the apparatus is reusable.

14. The apparatus of any of claim 1, wherein the ear device storage element stores and retains the device a stowed configuration when the ear device is not in use, and wherein the ear device is removable from the storage element when the ear device is in an in-use configuration.

15. The apparatus of claim 1, wherein the apparatus is configured such that when the ear device is stored in the ear device storage element, the ear device connection member is of similar length to a corresponding portion of the body attachment portion extending between the ear device storage element and the anchor point.

* * * * *